(12) United States Patent
Fuchs

(10) Patent No.: US 10,772,761 B2
(45) Date of Patent: Sep. 15, 2020

(54) CARTRIDGE DROP DISPENSER

(71) Applicant: F+K Innovationen Gmbh & Co. KG, Baden-Baden (DE)

(72) Inventor: Karl-Heinz Fuchs, Radolfzell (DE)

(73) Assignee: F+K INNOVATIONEN GMBH & CO. KG, Baden-Baden (DE)

( * ) Notice: Subject to any disclaimer, the term of this patent is extended or adjusted under 35 U.S.C. 154(b) by 0 days.

(21) Appl. No.: 16/087,779

(22) PCT Filed: Mar. 23, 2017

(86) PCT No.: PCT/EP2017/056954
§ 371 (c)(1),
(2) Date: Sep. 24, 2018

(87) PCT Pub. No.: WO2017/162805
PCT Pub. Date: Sep. 28, 2017

(65) Prior Publication Data
US 2019/0105195 A1    Apr. 11, 2019

(30) Foreign Application Priority Data

Mar. 23, 2016  (DE) .................. 10 2016 105 508
Aug. 4, 2016   (DE) .................. 10 2016 114 405

(51) Int. Cl.
| A61F 9/00  | (2006.01) |
| B05B 11/02 | (2006.01) |
| A61M 11/00 | (2006.01) |
| A61M 5/24  | (2006.01) |
| A61M 5/28  | (2006.01) |
| B01L 3/02  | (2006.01) |

(52) U.S. Cl.
CPC ......... *A61F 9/0008* (2013.01); *A61M 5/2425* (2013.01); *A61M 5/282* (2013.01); *A61M 11/007* (2014.02); *A61M 11/008* (2014.02); *B05B 11/025* (2013.01); *A61M 2210/0612* (2013.01); *B01L 3/0272* (2013.01)

(58) Field of Classification Search
CPC .. A61F 9/0008; A61M 11/007; A61M 11/008; A61M 5/2425; A61M 5/282; A61M 2210/0612; B05B 11/025; B01L 3/0272
See application file for complete search history.

(56) References Cited

U.S. PATENT DOCUMENTS

| 3,166,070 A  |   | 1/1965 | Everett |
| 4,344,573 A  |   | 8/1982 | De Felice |
| 5,810,778 A  | * | 9/1998 | Hjertman ............ A61M 5/1454 604/143 |
| 5,944,702 A  |   | 8/1999 | Py |

(Continued)

OTHER PUBLICATIONS

International search report for patent application No. PCT/EP2017/056954 dated Aug. 29, 2017.

*Primary Examiner* — Frederick C Nicolas
(74) *Attorney, Agent, or Firm* — Bachman & LaPointe, PC

(57) ABSTRACT

A cartridge droplet dosage device with a cartridge (1) and an actuation element (2), whereby the cartridge (1) includes a reservoir body (3), a cladding (5) and a plug (6), characterized in that a fluid groove (9) projects from the reservoir body (3) into an inner tube valve area (11), whereby the fluid groove (9) is releasable either by the yielding of a sealing rib (12) and/or by the yielding of a part of the cladding (5).

8 Claims, 14 Drawing Sheets

(56) References Cited

U.S. PATENT DOCUMENTS

| | | | | |
|---|---|---|---|---|
| 7,306,129 | B2* | 12/2007 | Swiss | B65D 47/205 |
| | | | | 137/853 |
| 7,571,838 | B2* | 8/2009 | Wolter | B05B 1/3431 |
| | | | | 222/320 |
| 7,798,185 | B2* | 9/2010 | Py | A45D 34/04 |
| | | | | 141/329 |
| 7,874,467 | B2* | 1/2011 | Pardes | A61F 9/0008 |
| | | | | 222/494 |
| 7,997,460 | B2* | 8/2011 | Pardes | B65D 47/205 |
| | | | | 137/853 |
| 8,100,295 | B2* | 1/2012 | Keller | B05C 17/00506 |
| | | | | 222/137 |
| 2007/0131721 | A1* | 6/2007 | Fritschi | A61M 5/28 |
| | | | | 222/391 |
| 2007/0257063 | A1 | 11/2007 | Schliemann | |
| 2010/0065049 | A1 | 3/2010 | Farieta et al. | |

* cited by examiner

CARTRIDGE DROP DISPENSER

BACKGROUND OF THE INVENTION

The invention relates to a cartridge droplet dosage device.

Multi-droplet dosage devices are known as systems from the prior art, which are placed onto containers such as bottles.

SUMMARY OF THE INVENTION

The object of the invention is to provide a cartridge droplet dosage device as a replaceable cartridge which can be placed by the user onto an actuation element. Here, the cartridge droplet dosage device should have an outlet which enables simple distribution, whereby the outlet is automatically re-closed and the interior space of the cartridge fully closes again.

The features disclosed herein lead to the attainment of the object. Advantageous designs are described herein and in the subclaims.

The idea lies in the storage of the fluid medicine in a replaceable cartridge with all the necessary functions, such as:

conservation-free storage, precise droplet generation, no dead volume that may become germ-infested or contaminated, mechanical, pressure-controlled outlet valve in connection with actuation that controls the distribution volume, and with a re-usable actuation element and medication that is usable for weeks after the package has been opened, so that the eye droplet product can be safely and effectively applied.

The droplet produced by the system should separate from the cartridge droplet surface in a pear-shaped form and leave behind no fluid residues on the drip off surface that may become germ-infested.

In order to easily detach droplets generated by the outlet valve from the drip off geometry, the valve gives the droplet volume that is becoming detached a slight acceleration due to the double-walled valve geometry.

The replaceable, double-walled cartridge is constructed as a longitudinal, cylindrical element, whereby the fluid reservoir, which in the open filling area of the cartridge is closed by a movable plug after the fluid has been filled, is arranged in the central axis.

In the device opposite the plug, the outlet valve geometry is integrated as a boundary of the cartridge.

The droplet outlet and droplet formation valve is designed as an inner tube valve, whereby the centric middle pin as an extension of the wall of the fluid reservoir functions as a valve support.

The inner tube valve is a valve model that can also be used with the known dosage pumps for the pharmaceutical and cosmetics industry as a dead volume-free, germ infestation-free outlet valve, and which can replace the ball outlet valves, pressure differentiation outlet valves and spring-balanced outlet valves available on the market.

Via the middle pin, a second flexible wall is fully mounted over the entire length of the cartridge in the form of a cylindrical cladding, whereby on the lower end of the cladding, the pin for affixing the cartridge in the actuation element is arranged.

Through the flexible, form-bound wall of the cladding in the upper valve area, the opening and closing force of the valve is controlled and adjusted.

The valve function is achieved by integrating a central longitudinal bore connected with a transverse bore to the outer diameter of the pin in the middle pin. Alternatively, on the outer diameter of the middle pin, one or more longitudinal grooves guides the fluid from the central fluid reservoir between the two walls of the pin and the cladding.

As a result of the displacement of the plug via the actuation element, the fluid in the reservoir is pressed over the feeds of the bores or grooves against the flexible wall of the cladding, so that the flexible wall expands.

Due to differing wall thicknesses and geometries, and the resulting system forces of the circumferential wall that are generated, the droplet volume which is being built up forces itself via the annular gap that forms between the two walls towards the system outlet.

As an additional seal, circumferential sealing grooves can be provided on the lower end of the pin or the cladding.

The valve outlet and the drip off surface is a planar surface which is created by the planar surface of the pin and the annular surface of the cladding.

The medium exits into the atmosphere in the geometric separation between the annular surface and the pin planar surface.

Due to the inherent tension of the flexible plastic cladding wall or valve wall, a rapid function reaction of the valve is achieved during closing and opening.

Also, due to the permanent play-free, circumferential cladding wall to the pin diameter, which is under pretension, a guaranteed contact of the cladding wall is guaranteed, so that no residual fluid or air can become trapped in the separation of the two walls and attract germs, since no air can penetrate into the system from the atmosphere.

Additionally, no contaminating germs can grow into the valve or system from the outside, and as a result, the user has the security of always applying clean medication.

Due to the geometry of the drip off planar surface, there are also no geometric recesses, edges, where residual fluids can settle and become contaminated by germs.

For additional protection during the storage of the product, the cartridge can be equipped with a protective cap.

Due to the double walls, including in the reservoir area, the diffusion resistance and light protection factor are increased, and as a result, more sensitive fluids can also be filled into the system, stored and given to the patient without preservation agents.

The replaceable cartridge is detachable anchored with the re-usable actuation element for application via a bayonet lock.

The actuation element with a three-point finger support can be designed as panel geometry or also as a complete sheath of the toothed piston which is injected as a perforation.

A partial area of the actuation element is the toothed piston with the finger support. The piston is connected opposite the finger support to the remaining actuation element body via a perforation, whereby the perforation breaks on first actuation and the piston is guided via the counter-tooth system on the actuation body to the lower planar surface of the system of the cartridge used.

The tooth system of the piston is structure such that for each tooth height and stroke the volume of a droplet, e.g. 30 µl, is forced in the reservoir towards the outlet of the cartridge.

Via the tooth ratcheting effect, the user hears and feels when they have pressed a droplet towards the system outlet when actuating the piston.

Due to the application on the eye, the patient cannot see when a droplet is available, which is why handling security is also offered to the user via the audible and palpable actuation process.

In order to equip the actuation element with a new cartridge, the piston pressed in the end position is turned into the retrieving position after removal of the used cartridge and is pulled back into the initial position.

As an alternative to the valve-closed system, an open system can also be produced with the same structure, whereby the outlet valve is replaced by a direct droplet outlet.

In order to protect the open cartridge against infestation with germs during storage before use with the alternative system, the protective cap required in use is injected on via a defined tear-off edge as product protection, with the closed side on the cartridge outlet side, so that the droplet exit is closed until application.

In other words, before the first usage of the system, the production protection is manually unscrewed by the user and replaced back as a protective cap after application.

Through the unscrewing of the product protection on the outlet opening of the cartridge, the droplet opening is opened for the application.

The geometry in the area of the outlet opening of the cartridge in combination with the injected product protection is a cylindrical, conical opening with a thin, conically running circumferential wall thickness for the targeted manual separation of the product protection.

The present invention with the preservative-free valve provides to the patient a system without conservation agents and without additional silver nitrate for the avoidance of germ infestation of the system. The patient receives the pure medication during application with a high level of handling security.

BRIEF DESCRIPTION OF THE DRAWINGS

Further advantages, features and details of the invention can be derived from the description of preferred exemplary embodiments below and with reference to the drawings, in which.

DETAILED DESCRIPTION

Figure 1:
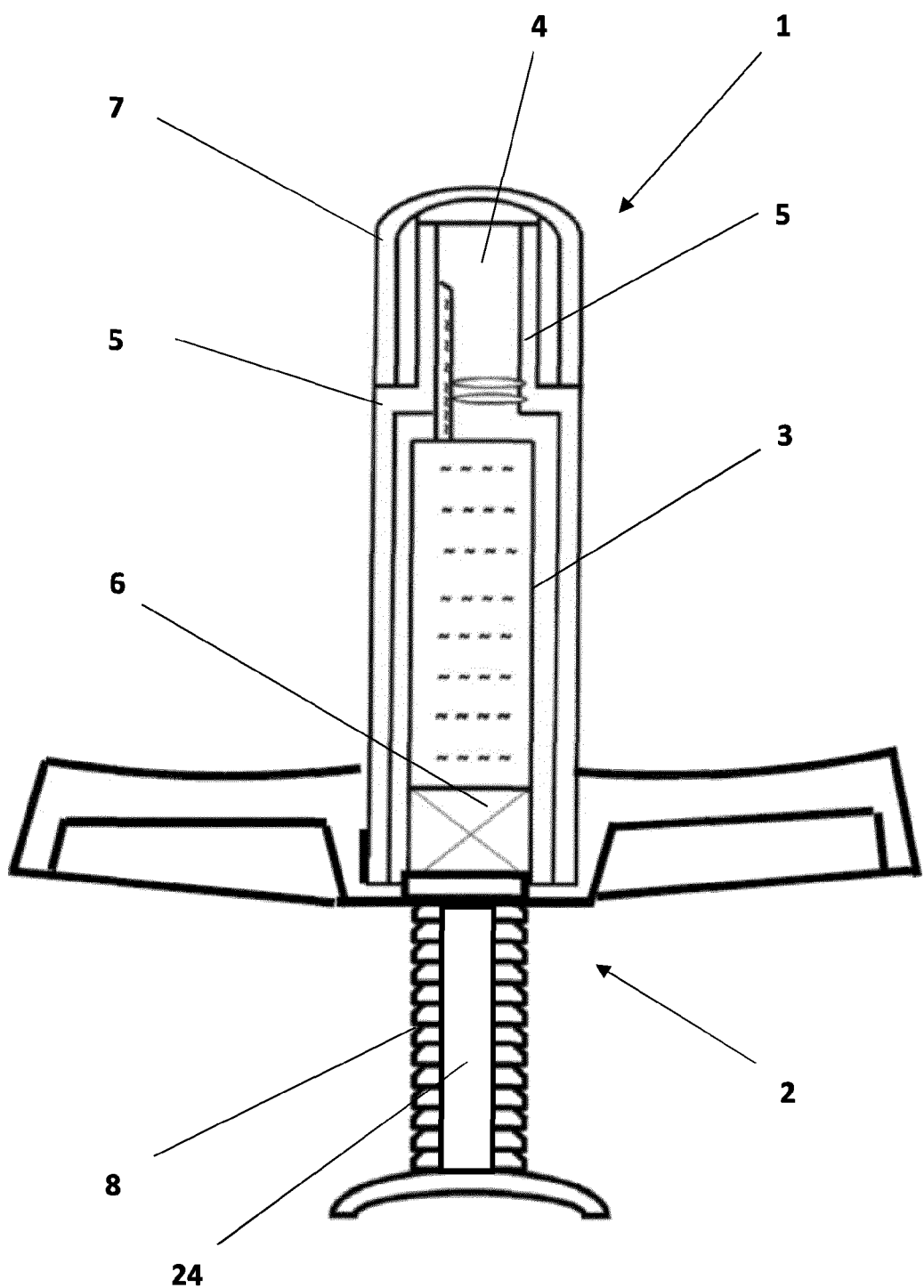
FIG. 1 shows a cross-section through the cartridge droplet dosage device according to the invention.

FIG. 1 shows a cross-section through the cartridge 1 and the actuation element 2.

The cartridge 1 consists of the reservoir body 3 with the valve pin 4 and the cladding 5, the plug 6 and the protective cap 7.

The actuation element 2 is a single piece with the perforated connected toothed piston 8 with the return groove 24.

Figure 2:
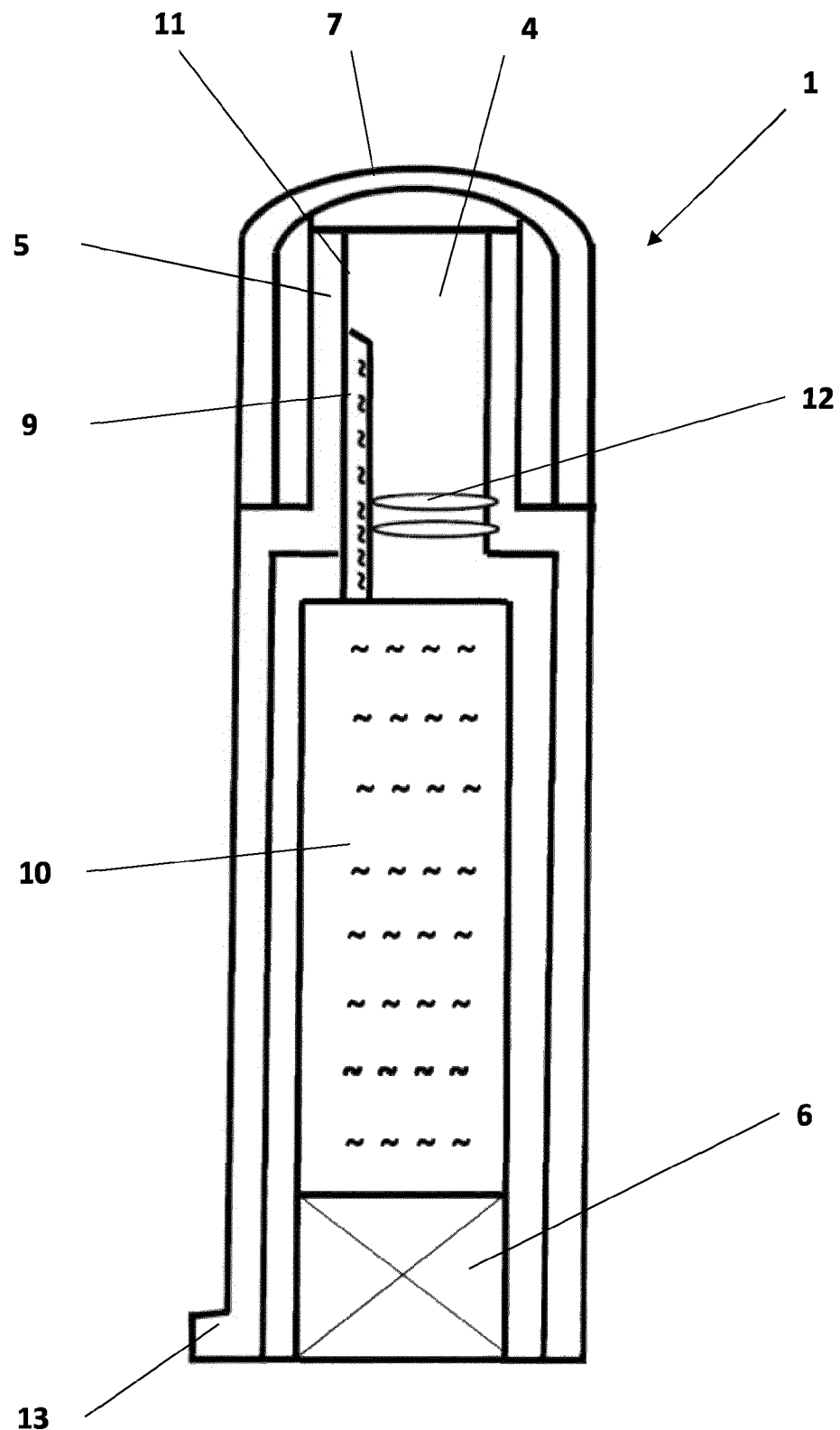
FIG. 2 shows a cross-section through the cartridge according to the invention.

FIG. 2 shows a cross-section through the cartridge 1 with protective cap 7, between the cladding wall 5 and the valve pin 4, the fluid groove 9 runs from the reservoir 10 into the inner tube valve area 11.

As an additional fluid seal, circumferential sealing ribs 12 are provided around the pin diameter.

In the area of the plug 6, on the cladding wall 5, the locking pin 13 is arranged between the cartridge 1 and the actuation element 2.

Figure 3:
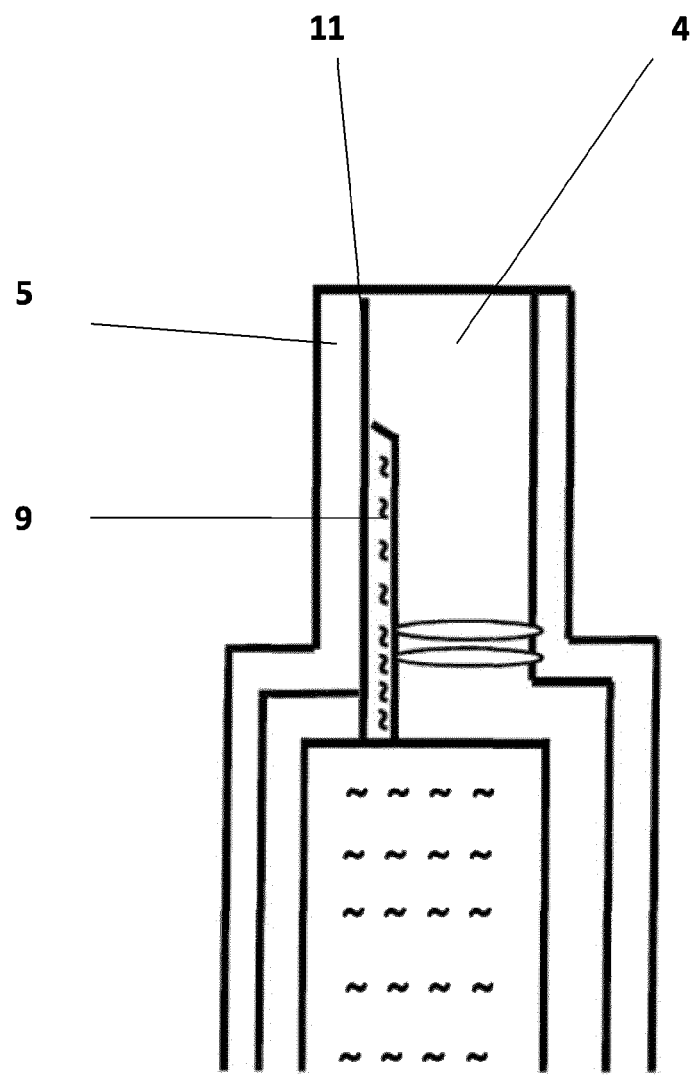
FIG. 3 shows a cross-section through the valve area of the cartridge according to the invention.

FIG. 3 shows a cross-section through the valve area 11 of the cartridge 1.

In the inner tube valve sealing area 11, the cladding wall 5 is in full contact with a slight pre-tension on the pin diameter 4.

The fluid groove 9 brings the medication to be applied to the sealing area 11, so that an annular gap is formed which allows the fluid to exit.

Figure 4:
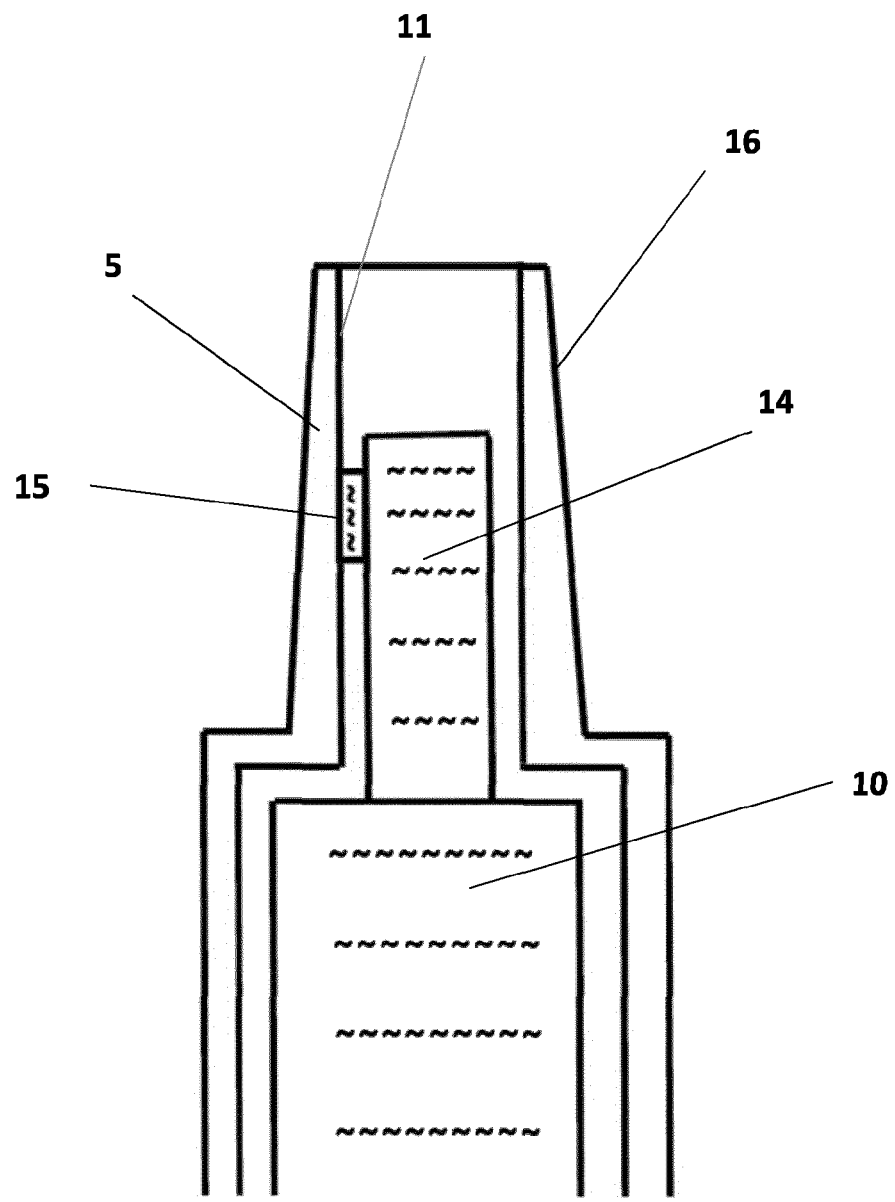
FIG. 4 shows a cross-section through an exemplary embodiment of the valve area of the cartridge according to the invention.

FIG. 4 shows a cross-section through a variant of the valve area 11 of the cartridge 1.

The central bore 14 supplies the transverse bore 15 from the fluid reservoir 10 with the medication to be distributed, in order to enable it to exit the cartridge as a droplet via the sealing area 11.

With the cladding geometry 16 of the cladding 5, the necessary sealing and opening forces of the inner tube valve are generated.

Figure 5:
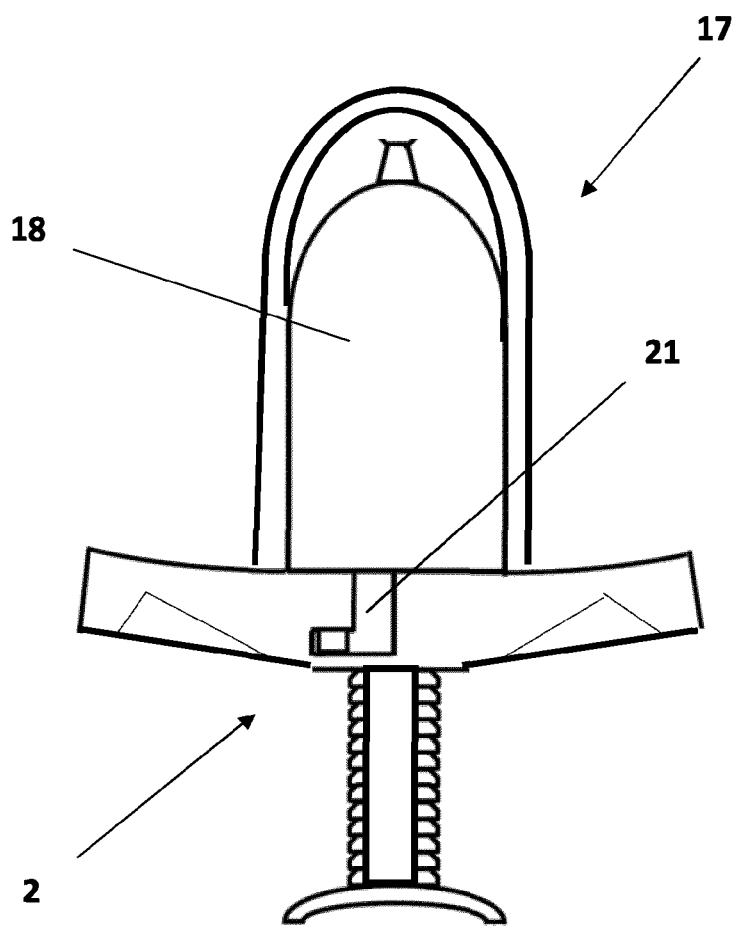
FIG. 5 shows a view of the open system with placed on protective cap.

FIG. 5 shows a view of the open system 17 with inserted open cartridge 18 and the actuation element 2 with the toothed piston 8.

The bayonet lock 21 is also shown.

Figure 6:
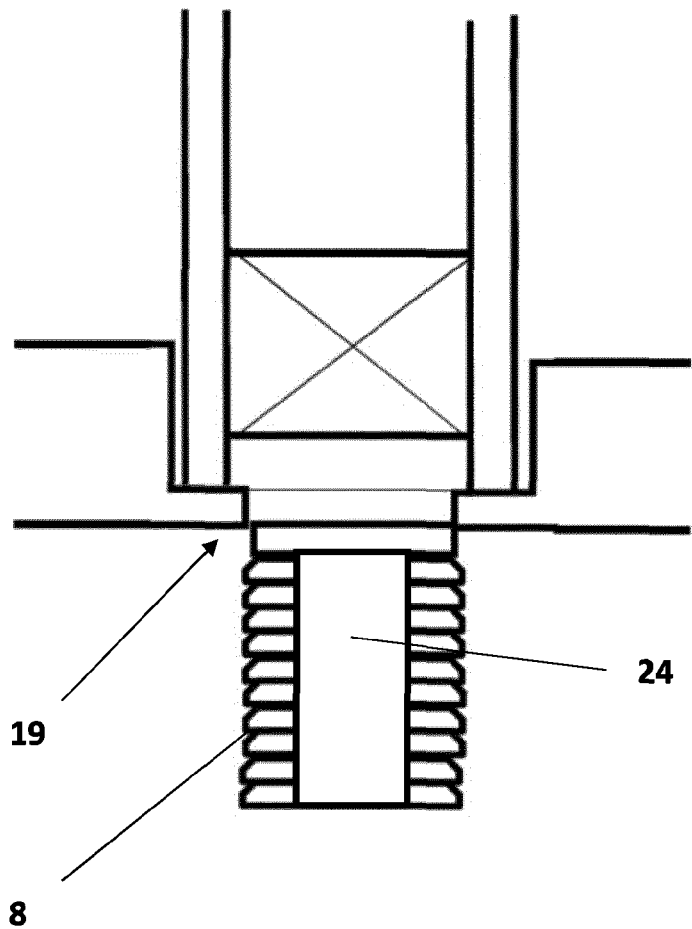
FIG. 6 shows a cross-section through the connection area of the toothed actuation piston.

FIG. 6 shows a cross-section through the perforation area 19 with the toothed piston 8 and the return groove 24.

Figure 7:
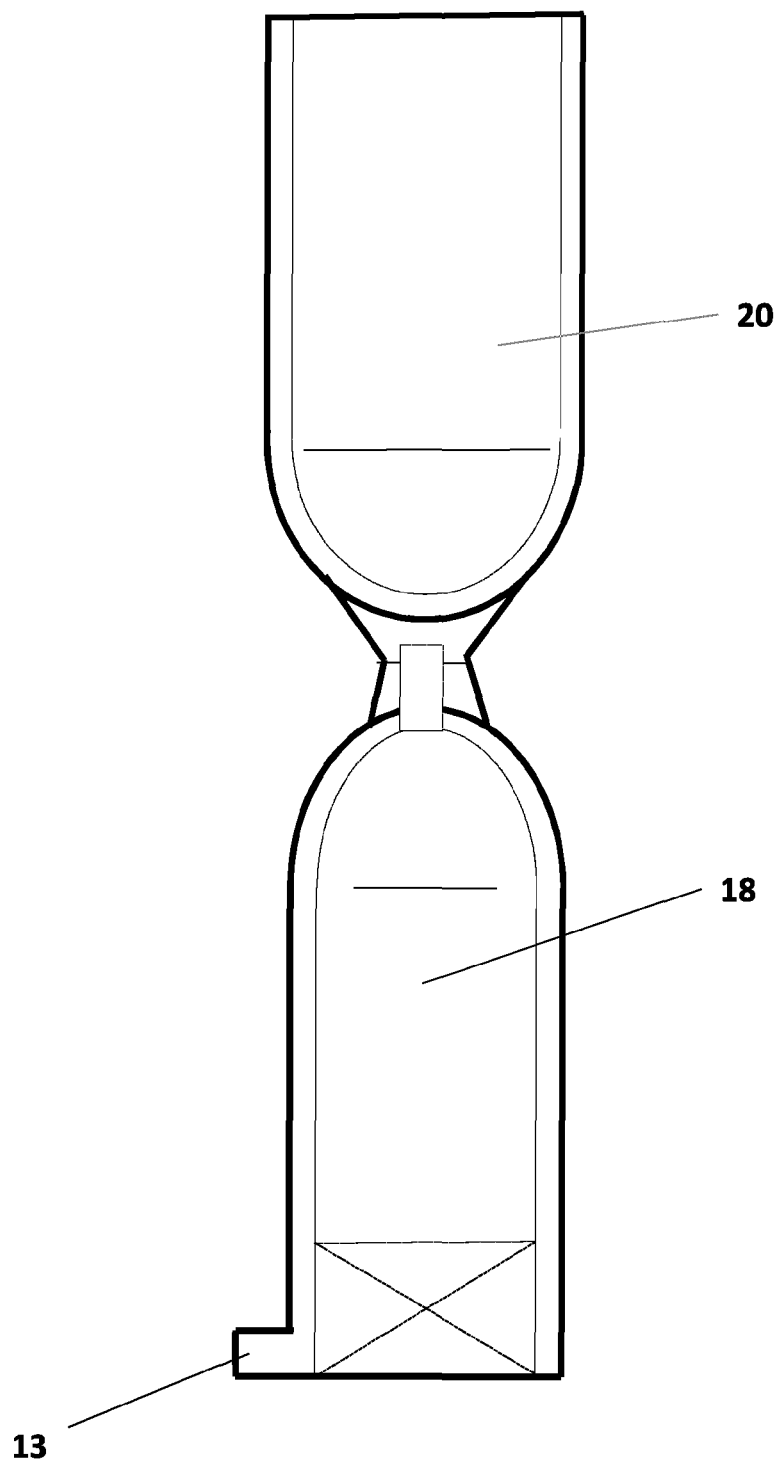
FIG. 7 shows a view of the cartridge with connected protective cap.

FIG. 7 shows a view of the open cartridge 18 with connected product protection/protective cap 20 and the locking pin 13.

Figure 8:
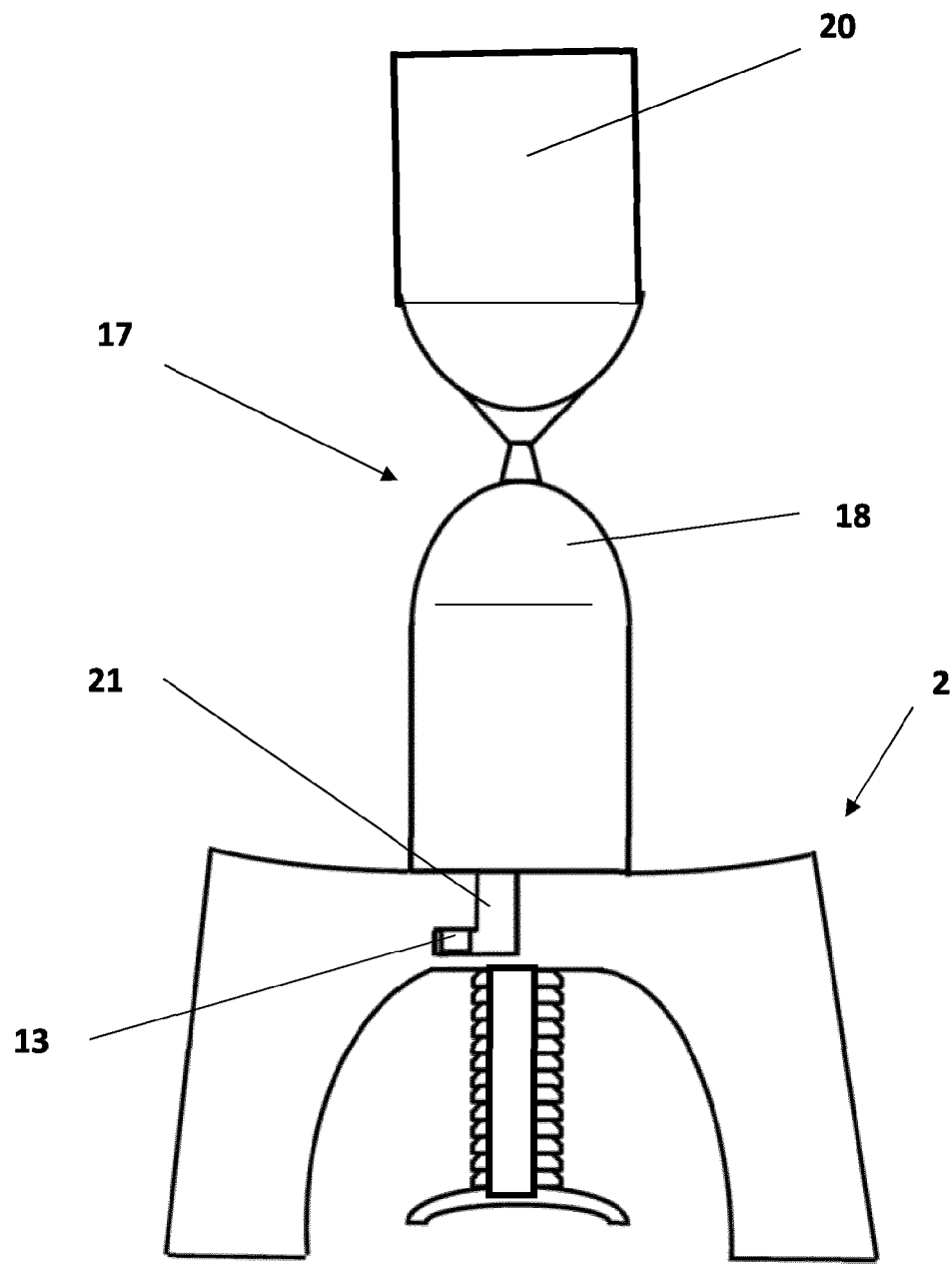
FIG. 8 shows a view of the open system with placed on cartridge.

FIG. 8 shows a view and variant of the open system with inserted cartridge 18 and product protection/protective cap 20 that has not yet been separated, as well as a geometric variant of the actuation protection 2 with the bayonet lock 21 and the locking pin 13.

Figure 9:
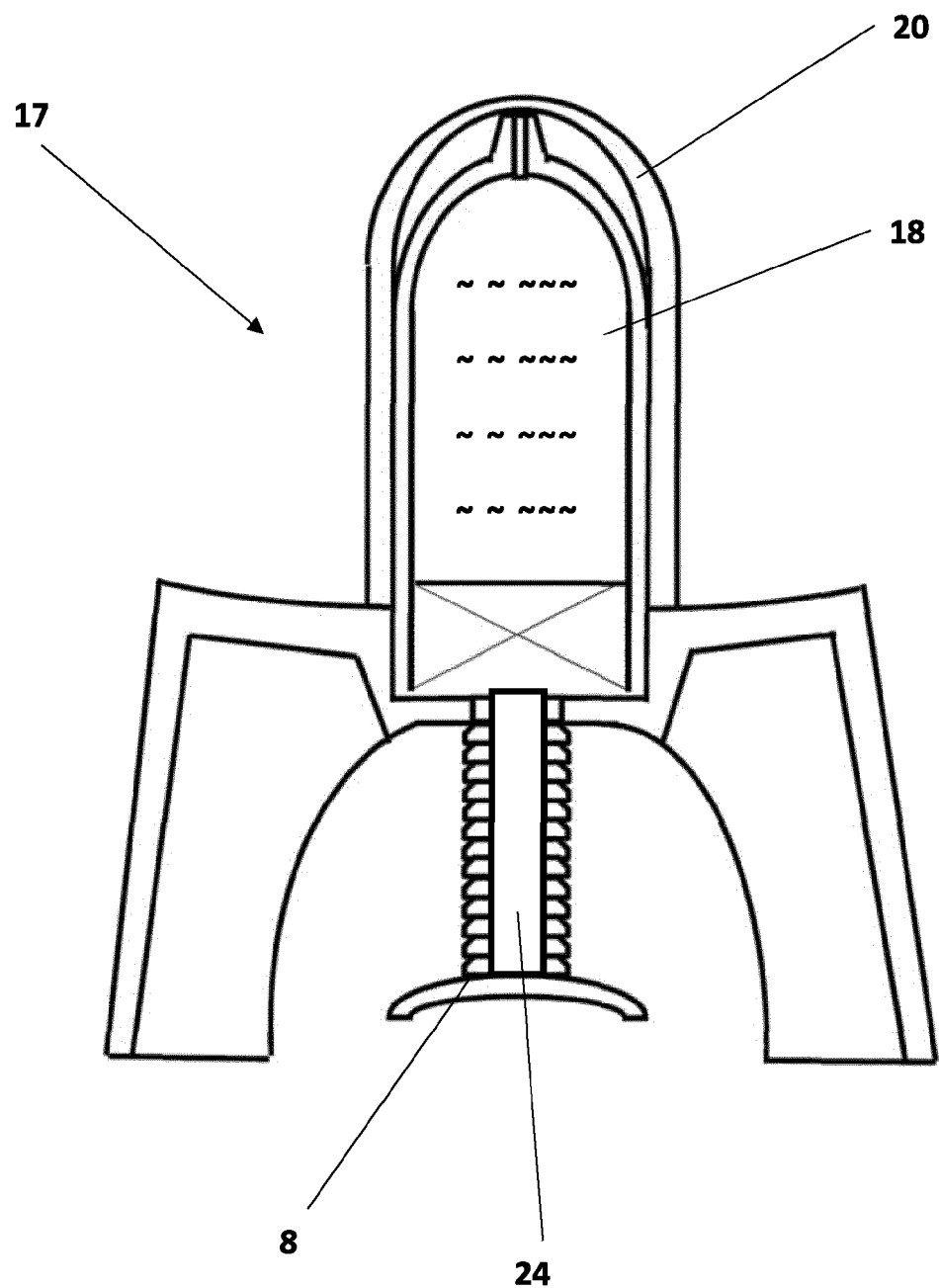
FIG. 9 shows a cross-section through the open system with placed on cartridge and attached protective cap.

FIG. 9 shows a cross-section through the open system with the geometric sheath variant of the piston 8 in the actuation element 2 and the attached protective cap 20 on the cartridge 18.

Figure 10:
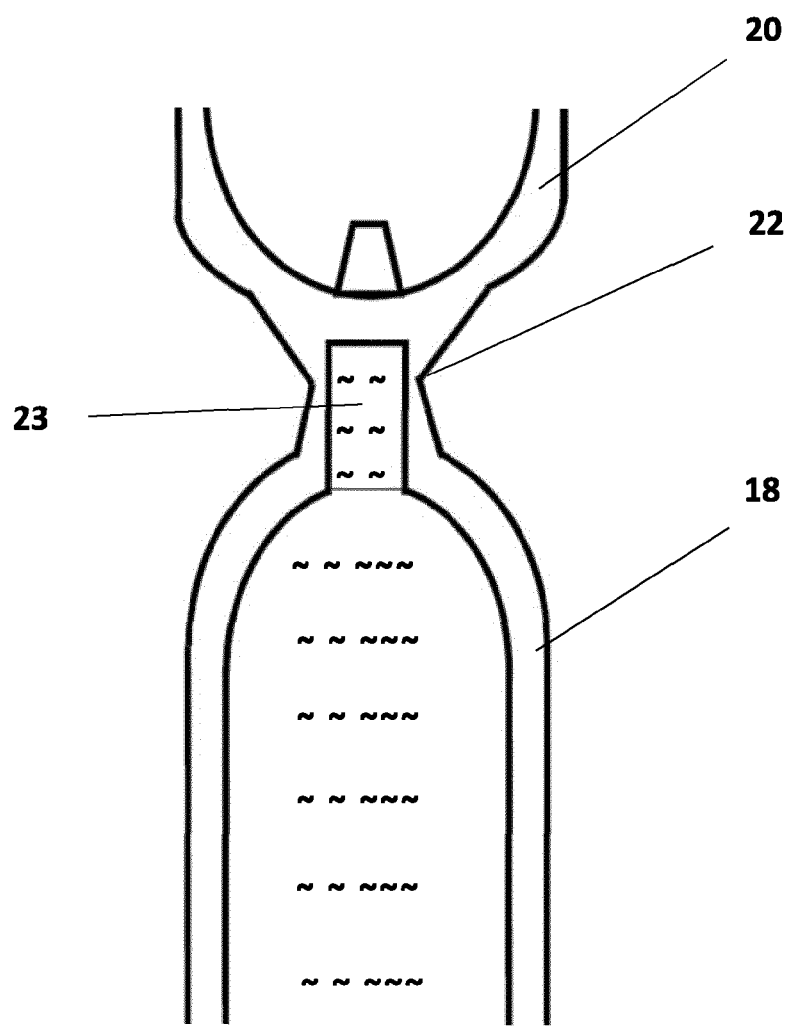
FIG. 10 shows a cross-section through the droplet outlet of the open system.

FIG. 10 shows a cross-section through a partial area of the open variant in the outlet of the cartridge 18 with the product protection/protective cap 20 not yet separated. The separation area 22 with the separation geometry opens the outlet bore 23 when the product protection is removed, which is then used as a protective cap 20.

Further exemplary embodiments are designed such that the inner tube valve area can be placed onto a standard pump system or directly onto a standard squeeze bottle.

The inner tube valve area according to the invention has fewer parts than the pump or squeeze system outlet valves known from the prior art.

The two-part valve system with the adapted pump or squeeze bottle system acts as a tight, non return-suction droplet dosage valve without dead space that is prone to becoming infested with germs.

Figure 11:
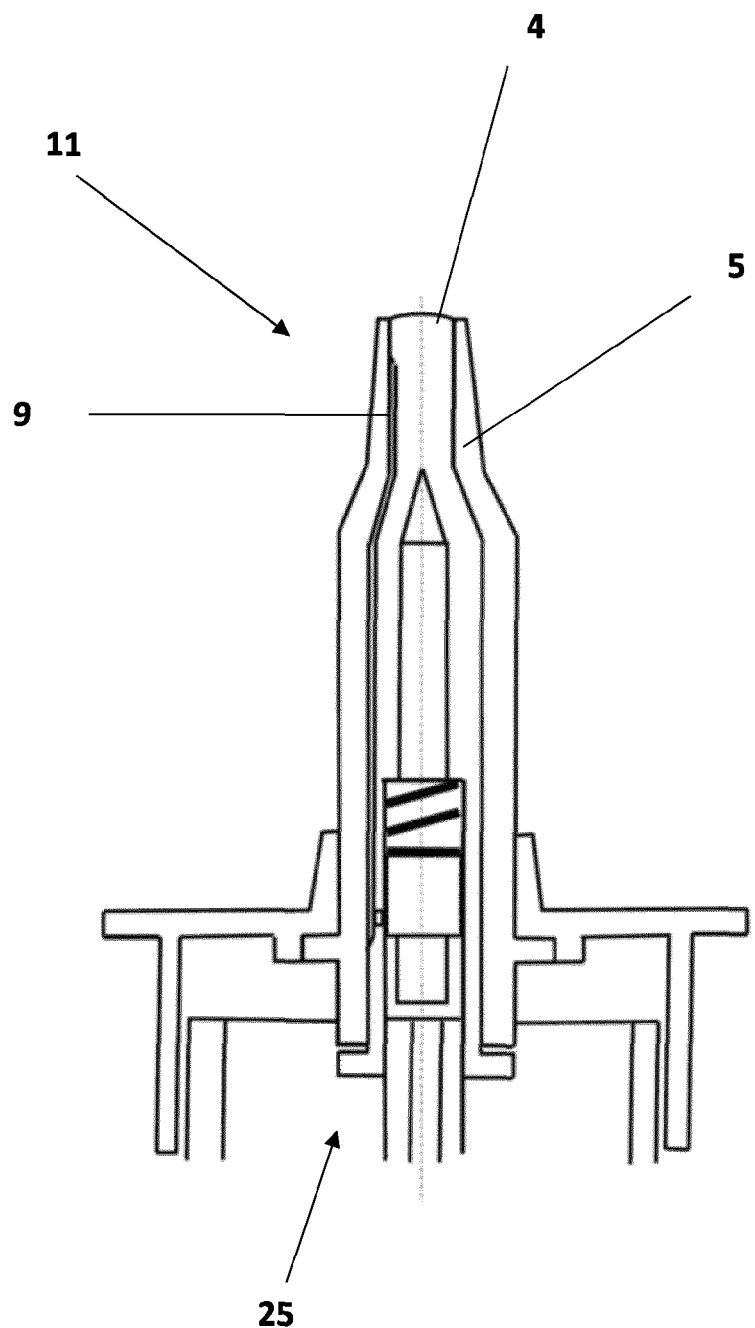
FIG. 11 shows a cross-section through a further exemplary embodiment of the inner tube valve area on a standard pump system.

FIG. 11 shows a cross-section of the inner tube valve area 11, the valve pin 4 with the fluid groove 9 and the cladding 5 on a standard pump system.

Figure 12:
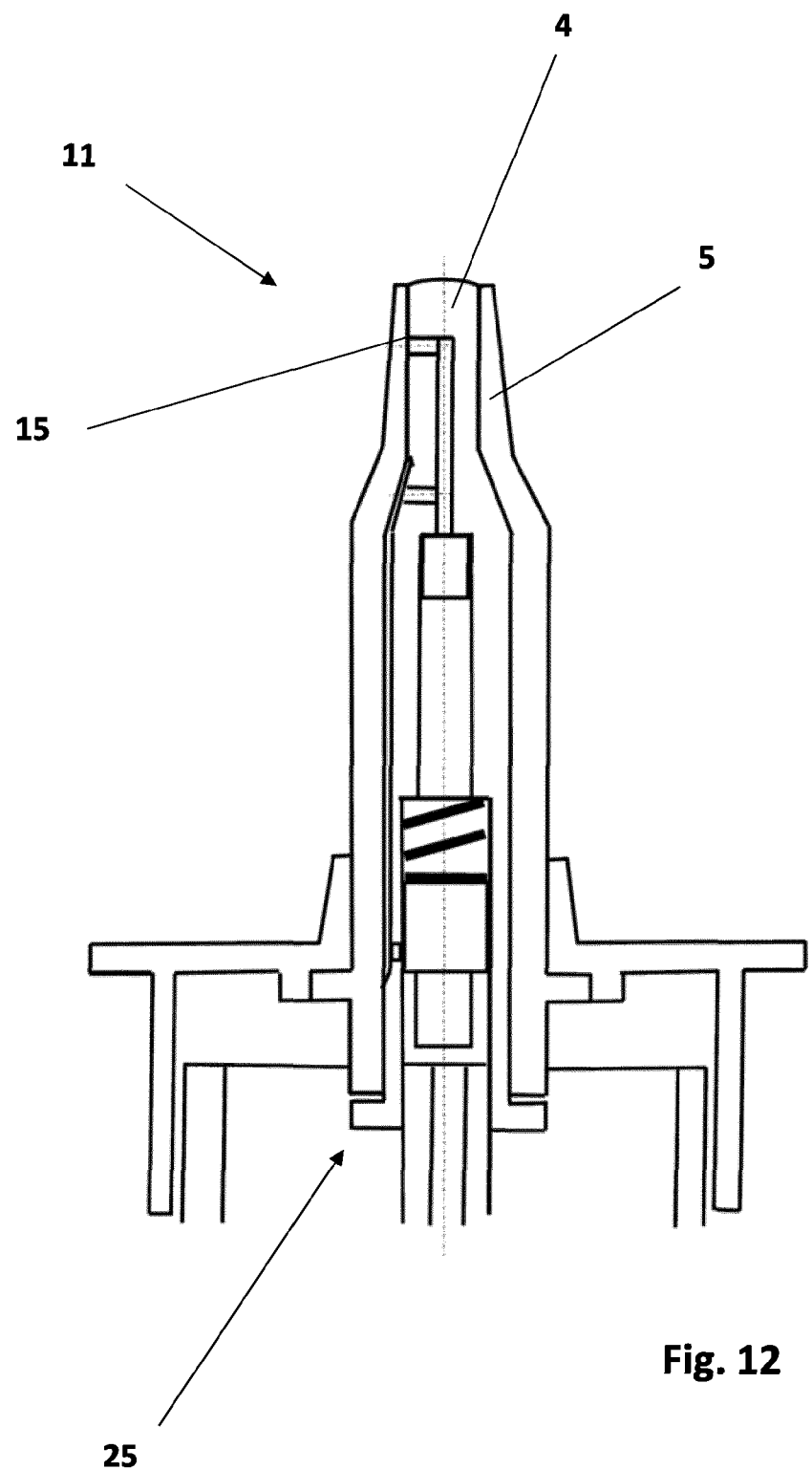
FIG. 12 shows a cross-section through a further exemplary embodiment of the inner tube valve area on a standard pump system.

FIG. 12 shows a cross-section of the inner tube valve area 11, the valve pin 4 with the transverse bore 15 and the cladding 5 on a standard pump system.

Figure 13:
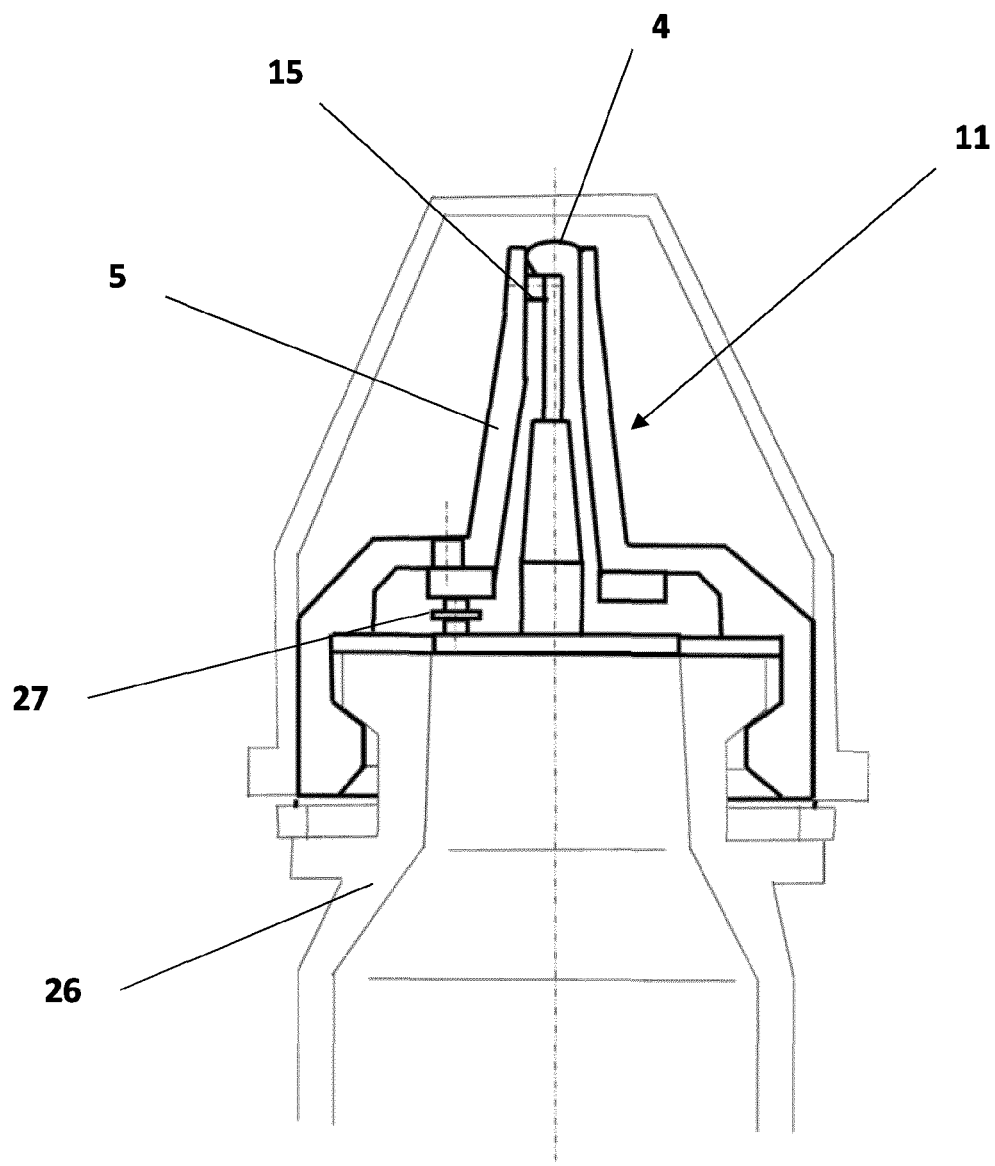
FIG. 13 shows a cross-section through a further exemplary embodiment of the inner tube valve area on a squeeze bottle.

FIG. 13 shows a cross-section of the inner tube valve area 11 on a squeeze bottle 26. The air compensation of the bottle is controlled via a filter 27. The cladding 5 has a snap lock on the bottle neck side and the valve pin 4 stands with an integrated flange on the bottle neck.

Figure 14:
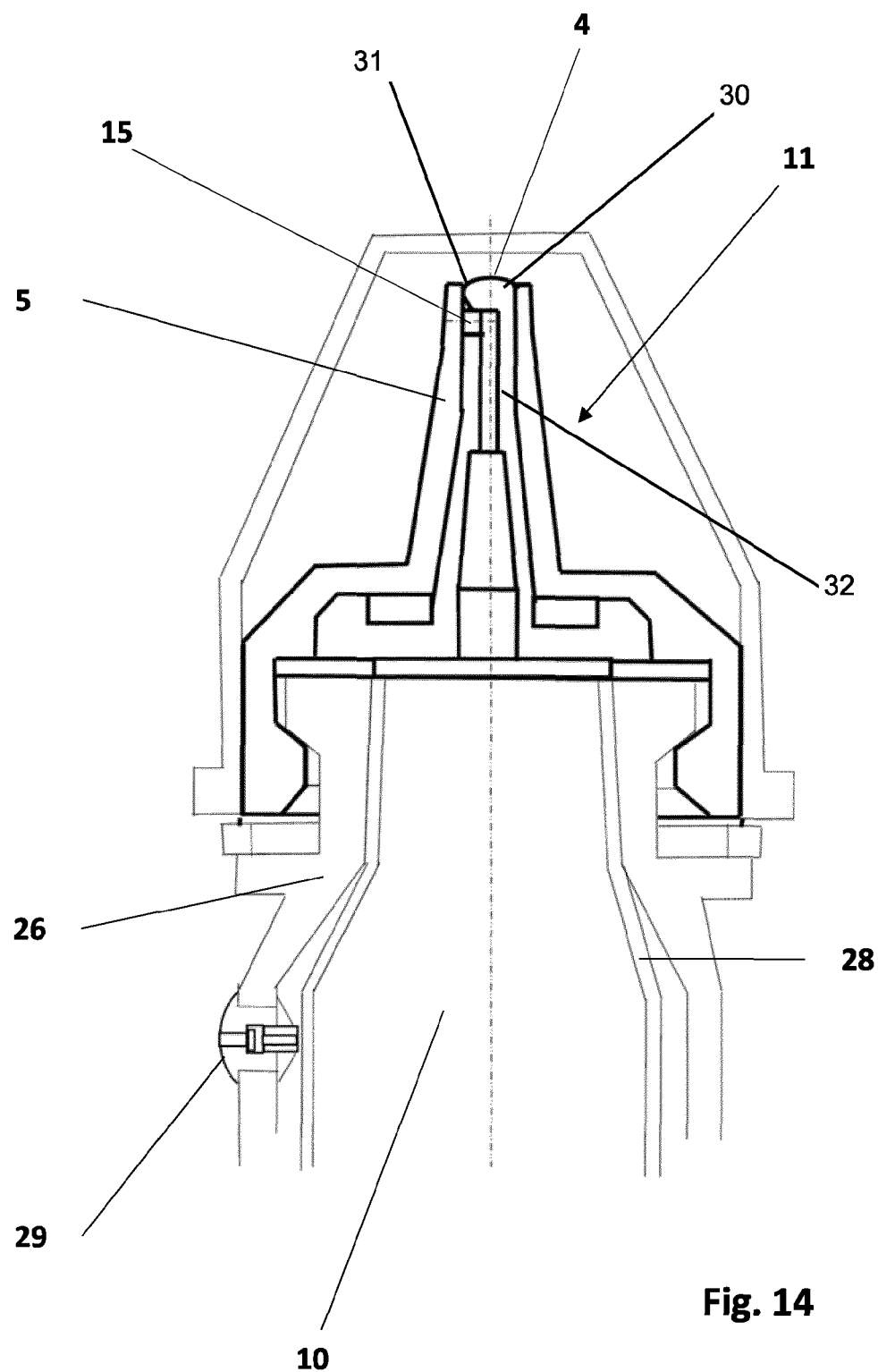
FIG. 14 shows a cross-section through a further exemplary embodiment of the inner tube valve area on a squeeze bottle with inner bag.

FIG. 14 shows a cross-section of the inner tube valve area 11 on a squeeze bottle 26 with an inner bag 28, the cladding 5 has a snap lock on the bottle neck side for anchoring with the bottle, and the valve pin 4 stands in an interactive connection with an integrated flange on the bottle neck. The valve pin 4 is arranged in the inner tube valve area 11, whereby the plate 30 on the side opposite the transverse bore 15 has a curve, and this curve has a bevel 31 in the area of the transverse bore 15.

Additionally, the plate 30 comprises a connecting piece 32, which extends from the plate 30 to the squeeze bottle 26, but which remains a part of the inner tube valve area 11. When fluid is distributed from the transfer bore 15, the bevel 31 is pushed aside by the fluid, and as soon as the pressure of the fluid lessens, the bevel 31 momentarily closes the outlet area.

The inner bag 28 preferably has a lower rigidity or hardness than the squeeze bottle 26, so that air flowing in through the plate valve 29 can be distributed around the inner bag 28 and said bag is drawn together according to the decreasing quantity of fluid in the fluid reservoir 10.

The system operates without air compensation in the fluid reservoir 10. Due to the vacuum created when the bottle is squeezed, the inner bag 26 is drawn together. In order to apply pressure to the inner bag 28 via the squeeze bottle 26, air or fluid flows between the inner bag and the bottle wall over a plate valve 29 integrated in the bottle wall. The plate valve 29 functions and closes off against the atmosphere, so that only medium between the inner bag and the bottle wall can flow in and not flow out.

The dosage droplet generation from a fluid reservoir 10 that is sealed against the atmosphere via the inner tube valve 11 in connection with a squeeze bottle 26, and in the bottle with an inner bag 28 that can be drawn together under vacuum, and the plate valve 29 integrated in the bottle wall, functions via the squeeze pressure, triggered by the pressing together of the bottle wall and the pressure that results on the inner bag 28.

The hollow space that is formed between the squeeze bottle 26 and the inner bag 28 through the removal of the droplet volume or removal of fluid from the inner bag 28 is used as a pressure store against the inner bag 28, whereby pressure is applied with compressed air due to the automatic closure of the plate valve 29 or with fluid against the bag wall through the squeezing of the bottle.

The droplet generation also functions with fluid in the hollow space between the squeeze bottle 26 and the inner bag 28 and under water or in fluid media.

The system with the inner tube valve area, the anchorage to the bottle and the inner bag as a fluid reservoir also remains one hundred percent tight during application and storage, so that even when applied over several weeks, no bacterial growth is possible in the system.

| List of reference numerals | |
|---|---|
| 1 | Cartridge |
| 2 | Actuation element |
| 3 | Reservoir body |
| 4 | Valve pin |
| 5 | Cladding |
| 6 | Plug |
| 7 | Protection cap |
| 8 | Piston |
| 9 | Fluid groove |
| 10 | Reservoir |
| 11 | Inner tube valve area |
| 12 | Sealing ribs |
| 13 | Locking pin |
| 14 | Central bore |
| 15 | Transverse bore |
| 16 | Cladding geometry |
| 17 | Open system |
| 18 | Open cartridge |
| 19 | Perforation area |
| 20 | Product protection/protective cap |
| 21 | Bayonet lock |
| 22 | Separation area |
| 23 | Outlet bore |
| 24 | Return groove |
| 25 | Pump system |
| 26 | Squeeze bottle |
| 27 | Filter |
| 28 | Inner bag |
| 29 | Plate valve |
| 30 | |
| 31 | |
| 32 | |
| 33 | |
| 34 | |
| 35 | |
| 36 | |
| 37 | |
| 38 | |
| 39 | |
| 40 | |
| 41 | |
| 42 | |
| 43 | |
| 44 | |
| 45 | |
| 46 | |
| 47 | |
| 48 | |
| 49 | |
| 50 | |
| 51 | |
| 52 | |
| 53 | |
| 54 | |
| 55 | |
| 56 | |
| 57 | |
| 58 | |
| 59 | |
| 60 | |
| 61 | |
| 62 | |
| 63 | |

| List of reference numerals |
|---|
| 64 |
| 65 |
| 66 |

The invention claimed is:

1. A cartridge droplet dosage device with a cartridge (1) and an actuation element (2), whereby the cartridge (1) comprises a reservoir body (3), a cladding (5) and a plug (6), wherein
a fluid groove (9) projects from the reservoir body (3) into an inner tube valve area (11), whereby the fluid groove (9) is releasable either by the yielding of a sealing rib (12) and/or by the yielding of a part of the cladding (5),
wherein the cartridge comprises a bayonet closure (13), whereby the bayonet closure (13) is connectable to a bayonet lock (21) of the actuation element (2),
wherein the actuation element (2) comprises a piston (8), whereby the piston (8) is actively connectable to the plug (6), and
wherein the actuation element (2) comprises a perforation area (19), whereby the perforation area (19) is arranged between the piston (8) and a counterpiece of the actuation element (2).

2. The cartridge droplet dosage device according to claim 1, wherein the sealing rib (12) and/or the cladding (5) is flexible under pressure and is resettable.

3. The cartridge droplet dosage device according to claim 1, wherein the cartridge (1) has a detachable product protection (20), whereby the product protection (20) also serves as protective cap.

4. A cartridge droplet dosage device with a cartridge (1) and an actuation element (2), whereby the cartridge (1) comprises a reservoir body (3), a cladding (5) and a plug (6), wherein
a central bore (14) projects from the reservoir body (3) into an inner tube valve area (11), whereby the central bore (14) is releasable by the yielding of a part of the cladding (5), whereby between the cladding (5) and the central bore (14) a transverse bore (15) is arranged, wherein the cladding (5) is flexible under pressure and is resettable,
wherein the actuation element (2) comprises a piston (8), whereby the piston (8) is actively connectable to the plug (6), and
wherein the actuation element (2) comprises a perforation area (19), whereby the perforation area (19) is arranged between the piston (8) and a counterpiece of the actuation element (2).

5. The cartridge droplet dosage device according to claim 4, wherein the cartridge comprises a bayonet closure (13), whereby the bayonet closure (13) is connectable to a bayonet lock (21) of the actuation element (2).

6. The cartridge droplet dosage device according to claim 4, wherein the cartridge (1) has a detachable product protection (20), whereby the product protection (20) also serves as protective cap.

7. A cartridge droplet dosage device with a cartridge (1) and an actuation element (2), whereby the cartridge (1) comprises a reservoir body (3), a cladding (5) and a plug (6), wherein
a fluid groove (9) projects from the reservoir body (3) into an inner tube valve area (11), whereby the fluid groove (9) is releasable either by the yielding of a sealing rib (12) and/or by the yielding of a part of the cladding (5),
wherein the cartridge comprises a bayonet closure (13), whereby the bayonet closure (13) is connectable to a bayonet lock (21) of the actuation element (2),
wherein the actuation element (2) comprises a piston (8), whereby the piston (8) is actively connectable to the plug (6), and
wherein the piston (8) has toothing.

8. A cartridge droplet dosage device with a cartridge (1) and an actuation element (2), whereby the cartridge (1) comprises a reservoir body (3), a cladding (5) and a plug (6), wherein
a central bore (14) projects from the reservoir body (3) into an inner tube valve area (11), whereby the central bore (14) is releasable by the yielding of a part of the cladding (5), whereby between the cladding (5) and the central bore (14) a transverse bore (15) is arranged, wherein the cladding (5) is flexible under pressure and is resettable,
wherein the actuation element (2) comprises a piston (8), whereby the piston (8) is actively connectable to the plug (6), and
wherein the piston (8) has toothing.

* * * * *